US012569463B2

(12) United States Patent
Dinarello et al.

(10) Patent No.: US 12,569,463 B2
(45) Date of Patent: Mar. 10, 2026

(54) METHOD FOR TREATING DIABETES

(71) Applicant: Olatec Therapeutics, Inc., New York, NY (US)

(72) Inventors: Charles A. Dinarello, Boulder, CO (US); Carlo Marchetti, Denver, CO (US); Marc Y. Donath, Rüschlikon (CH)

(73) Assignee: OLATEC THERAPEUTICS, INC., New York, NY (US)

( * ) Notice: Subject to any disclaimer, the term of this patent is extended or adjusted under 35 U.S.C. 154(b) by 689 days.

(21) Appl. No.: 17/934,526

(22) Filed: Sep. 22, 2022

(65) Prior Publication Data

US 2023/0028615 A1 Jan. 26, 2023

Related U.S. Application Data

(63) Continuation of application No. PCT/US2021/023497, filed on Mar. 22, 2021.

(60) Provisional application No. 62/994,486, filed on Mar. 25, 2020.

(51) Int. Cl.
*A61K 31/275* (2006.01)
*A61P 3/10* (2006.01)

(52) U.S. Cl.
CPC .............. *A61K 31/275* (2013.01); *A61P 3/10* (2018.01)

(58) Field of Classification Search
CPC ................................ A61K 31/275; A61P 3/10
See application file for complete search history.

(56) References Cited

U.S. PATENT DOCUMENTS

2019/0307718 A1* 10/2019 Marchetti ............ A61K 9/0053

FOREIGN PATENT DOCUMENTS

WO 2018204764 A1 11/2018
WO 2019023145 A1 1/2019

OTHER PUBLICATIONS

Huang et al., EMBO Molecular Med. (2018) (10), No. 4.*
Hua et al., Journal of Experimental Med. (2017)vol. 214, No. 11 pp. 3219-3238.*
Hua Jiang, et al., "Identification of a selective and direct NLRP3 inhibitor to treat inflammatory disorders", Journal of Experimental Medicine, vol. 214, No. 11, Oct. 11, 2017, pp. 3219-3238.
Huang Yi, et al., "3 to treat inflammasome-driven diseases", Embo Molecular Medicine, vol. 10, No. 4, Mar. 12, 2018, https:onlinelibrary.wiley.com/doi/full-XML/10.15252/emmm.201708689.
Hongbin He, et al., "Oridonin is a covalent NLRP3 inhibitor with strong anti-inflammasome activity", Nature Communications, vol. 9, No. 1, Dec. 1, 2018, https://www.nature.com/articles/s41467-018-04947-6.pdf.
Sujuan Ding, et al., "Modulatory Mechanisms of the NLRP3 Inflammasomes in Diabetes", Biomolecules, vol. 9, No. 12, Dec. 9, 2019, p. 850.
Webmd, "Insulin Resistance", Jul. 1, 2019, https://www.webmd.com/diabetes/insulin-resistance-syndrome.
United States Patent & Trademark Office (USPTO), International Search Report, PCT/US2021/023497, Jun. 8, 2021.
European Patent Office, Extended European Search Report, EPO Application No. 21774979.5, Mar. 27, 2024.
Jansen, TL et al., "P160 The first phase 2A proof-of-concept study of selective NLRP3 inflammasome inhibitor, dapansutrile (OLT1177), in acute gout", Annals of the Rheumatic Diseases, Mar. 2019, A70-A71, vol. 78, Supplement 1, Elsevier B.V.
Zahid, Ayesha et al., Pharmacological Inhibitors of the NLRP3 Inflammasome, Frontiers in Immunology, Oct. 25, 2019, pp. 1-10, vol. 10, Article 2538.
Lee, Hye-Mi et al., Upregulated NLRP3 Inflammasome Activation in Patients with Type 2 Diabetes, Diabetes A Journal of the American Diabetes Association, Jan. 1, 2013, pp. 194-204, vol. 62, Issue 1, American Diabetes Association.
Schroder, Kate et al., The NLRP3 Inflammasome: A Sensor for Metabolic Danger?, Science, Jan. 15, 2010, pp. 296-300, vol. 327, No. 5963, American Association forthe Advancement of Science.
Sharma, Arpeeta et al., Oxidative Stress and NLRP3-Inflammasome Activitiy as Significant Drivers of Diabetic Cardiovascular Complications: Therapeutic Implications, Frontiers in Physiology, Feb. 20, 2018, vol. 9, Article 114.

* cited by examiner

*Primary Examiner* — Paul V Ward
(74) *Attorney, Agent, or Firm* — Perkins Coie LLP; Viola T. Kung

(57) ABSTRACT

The present invention is directed to a method for treating diabetes. The method comprises administering to a subject in need thereof dapansutrile, or a pharmaceutically acceptable solvate thereof, in an effective amount. Oral administration is a preferred route of administration.

8 Claims, 2 Drawing Sheets

STUDY PROCEDURES

Screening/ Day 1
- Consent
- Eligibility
- History
- Physical Exam
- Medication List
- Vital Signs x 2
- Labs x 2
- BIA
- Echocardiography
- CPX
- Questionnaires
- Dispensing

Day 4
- Vital Signs
- Med List
- Labs
- ECG
- Adherence

Day 8
- Vital Signs
- Med List
- Labs
- ECG
- Adherence

Day 14
- Physical Exam
- Vital Signs
- Medication List
- Labs
- BIA
- Echocardiography
- CPX
- Questionnaires
- Adherence

Day 28
- Physical Exam
- Vital Signs
- Medication List
- Labs
- BIA
- Echocardiography
- CPX
- Questionnaires
- Diary

Day 42
- Telephone

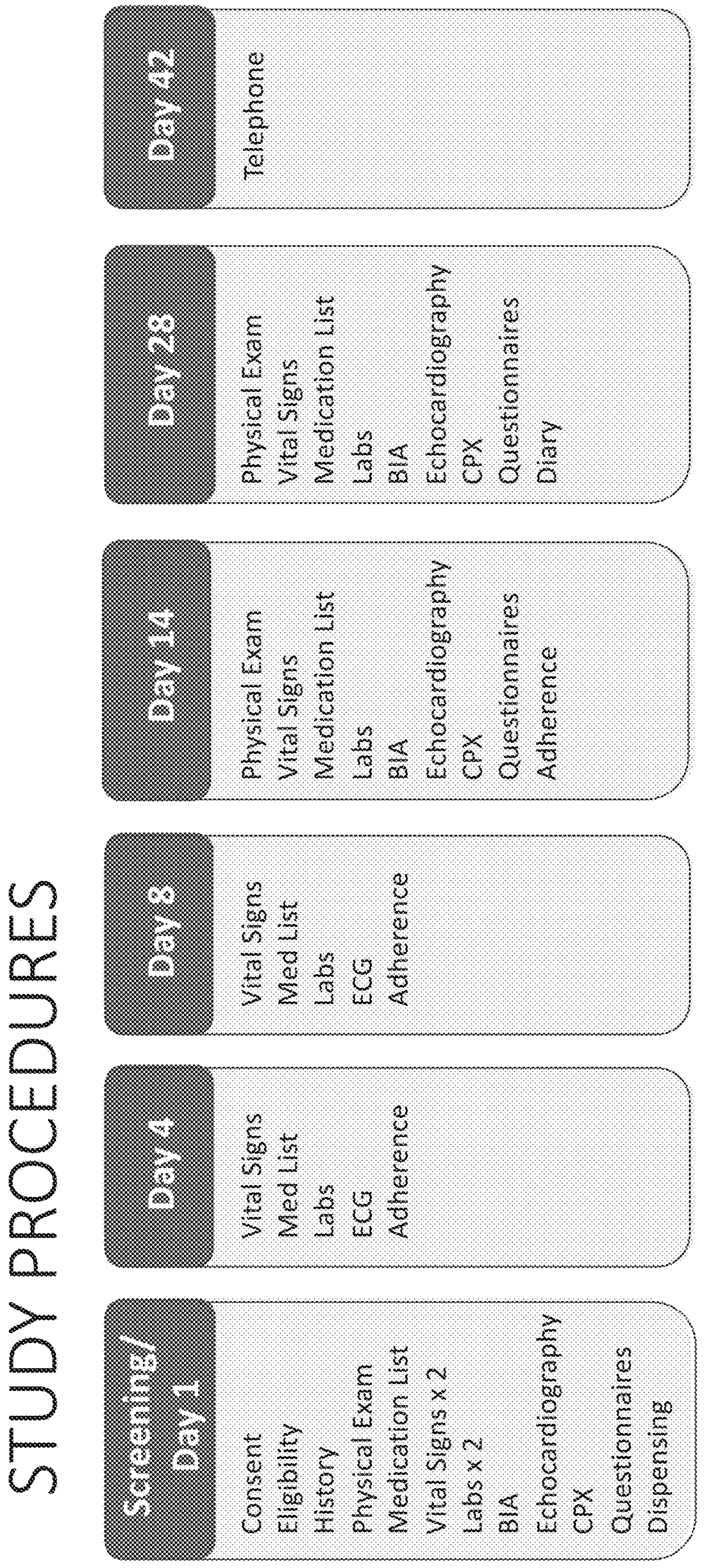

FIG. 2

METHOD FOR TREATING DIABETES

This application is a continuation of PCT/US2021/023497, filed Mar. 22, 2021; which claims the benefit of U.S. Provisional Application No. 62/994,486, filed Mar. 25, 2020. The contents of the above-identified applications are incorporated herein by reference in their entireties.

FIELD OF THE INVENTION

The present invention relates to using dapansutrile, or its pharmaceutically acceptable solvates, for treating diabetes.

BACKGROUND

Diabetes mellitus is a major public health problem. In the United States, there are over 10 million patients with diabetes. Diabetes is a syndrome that is caused by a relative or an absolute lack of insulin. Clinically, it is characterized by symptomatic glucose intolerance as well as alterations in lipid and protein metabolism. The maintenance of normal blood sugar levels is achieved by the actions of several hormones, most notably insulin, but also glucagon, epinephrine, corticosteroids, and growth hormone. Hyperglycemia is exemplified by higher than normal concentrations of glucose in the blood. The pancreas produces insulin which is released in response to increased blood glucose concentrations. Insulin works to lower the blood sugar levels by stimulating the uptake of glucose by cells. Glucose is used in cellular metabolism to produce energy, or is converted to glycogen for storage in the liver and muscles, or is used in the production of triglycerides and fats.

In patients with type 2 diabetes (T2D), the rates of heart failure, cardiovascular morbidity, renal dysfunction and retinopathy are unacceptably elevated. Heart failure occurs earlier than myocardial infarction or stroke as a T2D complication. Nephropathy is the major cause for dialysis and renal transplantation in patients with T2D. Retinopathy often requires irksome intra-ocular injections and is the leading cause for blindness in western societies for decades.

Current antidiabetic drugs primarily act as glucose lowering medications without directly targeting microvascular inflammation which has been demonstrated as a key factor in the development of the above-mentioned complications.

Activation of the innate immune system is apparent at all stages of the development of diabetes and its complications. This includes impaired (3-cell function, insulin resistance, cardiovascular diseases, heart failure, non-alcoholic steatohepatitis, nephropathy, polyneuropathy, fatigue, and retinopathy and macular oedema.

Pathological activation of the immune system plays a critical role in an increasing number of diseases and some of them are associated with diabetes, such as rheumatoid arthritis, gout, psoriasis and cancer.

To treat diabetes related conditions, several drugs are prescribed in addition to glucose lowering drugs. This multi-drug approach is often associated with decreased patient compliance, as the number of pills prescribed is inversely proportional to the adherence to treatment.

There is a need for an effective method to treat diabetes; the method should not only palliate hyperglycemia but also prevent disease progression, and beneficially target diabetic micro- and macrovascular complications.

BRIEF DESCRIPTION OF THE DRAWINGS

FIG. 2 shows the study procedures of Example 1.

DETAILED DESCRIPTION OF THE INVENTION

Figure 1:
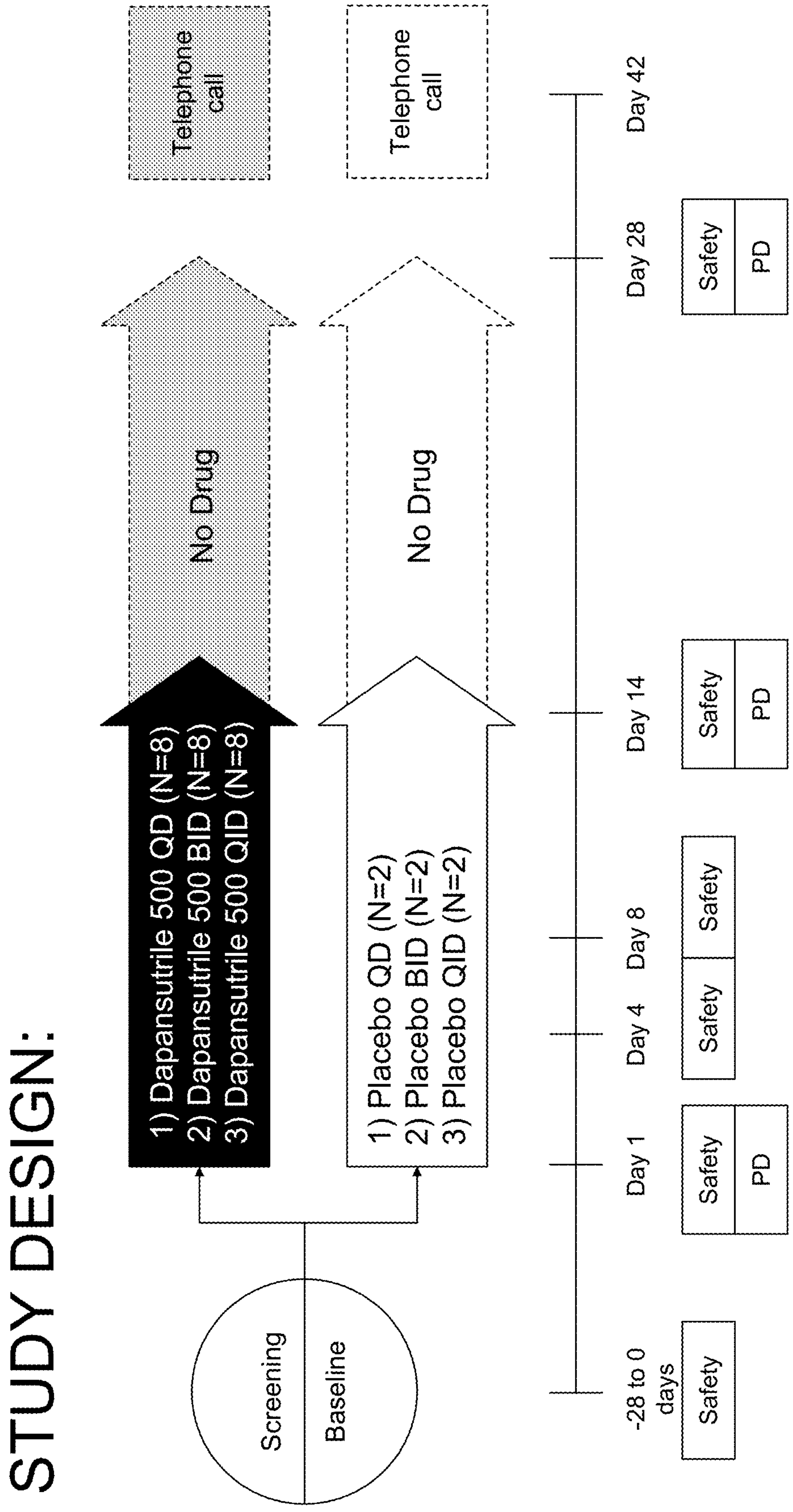
FIG. 1 shows the study design of Example 1. Cohort 1 were treated with 500 mg daily, Cohort 2 were treated with 500 mg twice a day, and Cohort 3 were treated with 500 mg 4 times a day, from Day 1 to Day 14. Pharmacodynamic (PD) study was done on Days 1, 14, and 28; that is, blood and urine were drawn and tested for biomarkers, including exvivo analyses.

The present invention is directed to a method for treating diabetes, in particular type 2 diabetes (T2D), which increases the rates of heart failure, cardiovascular morbidity, renal dysfunction and retinopathy. The present method not only lowers the blood glucose level in patients, but also prevents disease progression by treating microvascular inflammation in patients.

The method comprises the step of administering an effective amount of dapansutrile, or a pharmaceutically acceptable solvate thereof, to treat diabetes.

Dapansutrile inhibits the oligomerization of the NLRP3 inflammasome, which in turn prevents the activation of caspase-1 and the maturation of pro-IL-1β and pro-IL-18 to their active forms IL-1β and IL-18, respectively. The inventor has discovered that dapansutrile is effective in lowering blood glucose level in patients with diabetes. Dapansutrile targets IL-1 in patients with metabolic syndrome and T2D, which not only improves glycaemia, but at the same time prevents microvascular and cardiovascular morbidity.

Compound

The present invention uses a purified compound of dapansutrile (3-methanesulfonylpropionitrile), or a pharmaceutically acceptable solvate thereof:

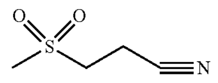

"Pharmaceutically acceptable solvates," as used herein, are solvates that retain the desired biological activity of the parent compound and do not impart undesired toxicological effects. Solvates are addition complexes in which the compound is combined with an acceptable co-solvent in some fixed proportion. Co-solvents include, but are not limited to, water, ethyl acetate, lauryl lactate, myristyl lactate, cetyl lactate, isopropyl myristate, methanol, ethanol, 1-propanol, isopropanol, 1-butanol, isobutanol, tert-butanol, acetone, methyl ethyl ketone, acetonitrile, benzene, toulene, xylene (s), ethylene glycol, dichloromethane, 1,2-dichloroethane, N-methylformamide, N,N-dimethylformamide, N-methylacetamide, pyridine, dioxane, and diethyl ether.

Pharmaceutical Compositions

The present invention provides pharmaceutical compositions comprising one or more pharmaceutically acceptable carriers and an active compound of dapansutrile, or a pharmaceutically acceptable salt, or a solvate thereof. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w), for a topical formulation; about 0.1-5% for an injectable formulation, 0.1-5% for a patch formulation, about 1-90% for a tablet formulation, and 1-100% for a capsule formulation. The active compound used in the pharmaceutical composition in general is at least 90%, preferably 95%, or 98%, or 99% (w/w) pure.

In one embodiment, the pharmaceutical composition is in a dosage form such as tablets, capsules, granules, fine granules, powders, syrups, suppositories, injectable solutions, patches, or the like. In another embodiment, the active compound is incorporated into any acceptable carrier, including creams, gels, lotions or other types of suspensions that can stabilize the active compound and deliver it to the affected area by topical applications. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone (polyvinylpyrrolidone), propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Method of Use

The present invention is directed to a method of treating diabetes. The method comprises the steps of first identifying a subject suffering from diabetes, and administering to the subject dapansutrile, in an amount effective to treat diabetes. "An effective amount," as used herein, is the amount effective to treat a disease by ameliorating the pathological condition or reducing the symptoms of the disease.

In one embodiment, the method lowers the fasting blood glucose level in a patient.

In one embodiment, the method lowers hemoglobin A1C (HbA1c) level in the blood.

In one embodiment, the method increases glucose uptake and regulates blood glucose.

In one embodiment, the method lowers the average level of blood sugar over the past 2 to 3 months in a patient.

In one embodiment, the method increases glucose uptake and regulates blood glucose level in a patient.

The pharmaceutical composition of the present invention can be applied by systemic administration and local administration. Systemic administration includes oral, parenteral (such as intravenous, intramuscular, subcutaneous or rectal), and other systemic routes of administration. In systemic administration, the active compound first reaches plasma and then distributes into target tissues. Local administration includes topical administration.

Dosing of the composition can vary based on the extent of the disease and each patient's individual response. For systemic administration, plasma concentrations of the active compound delivered can vary; but are generally 0.1-1000 μg/mL or 1-100 μg/mL.

In one embodiment, the pharmaceutical composition is administrated orally to the subject. The dosage for oral administration is generally at least 1 mg/kg/day and less than 100 mg/kg/day. For example, the dosage for oral administration is 1-100, or 5-50, or 10-50 mg/kg/day, for a human subject. For example, the dosage for oral administration is 100-10,000 mg/day, and preferably 500-2000, 500-4000, 500-4000, 1000-5000, 2000-5000, 2000-6000, or 2000-8000 mg/day for a human subject. The drug can be orally taken once, twice, three times, or four times a day. The patient is treated daily for 1 month, 2 month, o4 3 month, or up to the lifespan of the patient. For example, the patient is treated for 3-6 months, 3-9 months, or 6-12 months.

In one embodiment, the pharmaceutical composition is administrated intravenously to the subject. The dosage for intravenous bolus injection or intravenous infusion is generally 0.03 to 20 or 0.03 to 10 mg/kg/day.

In one embodiment, the pharmaceutical composition is administrated subcutaneously to the subject. The dosage for subcutaneous administration is generally 0.3-20 or 0.3-3 mg/kg/day.

Those of skill in the art will recognize that a wide variety of delivery mechanisms are also suitable for the present invention.

The present invention may be used in combination with one or more other treatments that lower blood glucose level.

The present invention is useful in treating a mammal subject, such as humans, horses, cows, dogs, and cats. The present invention is particularly useful in treating humans.

The following examples further illustrate the present invention. These examples are intended merely to be illustrative of the present invention and are not to be construed as being limiting.

EXAMPLES

Example 1. Clinical Study of Orally Administered Dapansutrile Capsules in Subjects with NYHA II-III Systolic Heart Failure Methodology The study was a single center, randomized, double-blinded, dose escalation trial to evaluate safety and pharmacodynamics of orally administered dapansutrile capsules in subjects with NYHA II-III systolic heart failure.

Main Criteria for Inclusion:

- Male and female subjects 18 years old or older
- Symptomatic stable heart failure (NYHA class II-III) with reduced left ventricular ejection fraction (LVEF≤40%, measured within 6 months of enrollment—no changes in cardiac medications or new device implantation within past 2 months)
- Peak exercise limited by shortness of breath and associated with a respiratory exchange ratio (RER)>1.00 (reflecting maximal aerobic effort)
- Reduced peak aerobic exercise capacity (peak V02) to less than 80% of predicted value by age/gender at Baseline
- Plasma CRP or hsCRP levels >2 mg/L at Screening
- Acceptable overall medical condition to be safely enrolled in and to complete the study (with specific regard to cardiovascular, renal and hepatic conditions) in the opinion of the Principal Investigator
- Ability to provide written, informed consent prior to initiation of any study-related procedures, and ability, in the opinion of the Principal Investigator, to understand and comply with all the requirements of the study Main Criteria for Exclusion:

- Women of childbearing potential, or men whose sexual partner(s) is a woman of childbearing potential who:
  - Are or intend to become pregnant (including use of fertility drugs) during the study
  - Are nursing
  - Are not using an acceptable, highly effective method of contraception until all follow-up procedures are complete
- Abnormal blood pressure or heart rate response, angina or ECG changes (ischemia or arrhythmias) occurring during CPX
- Presence or known history of autoimmune conditions
- Active or recent (within 2 weeks) infection prior to the Baseline visit
- History of or known positive for HIV, Hepatitis B surface antigen or antibodies to Hepatitis C Virus
- Any other concomitant medical or psychiatric condition, disease, or prior surgery that, in the opinion of the Principal Investigator, would impair the subject from safely participating in the trial and/or completing protocol requirements
- Known history of renal impairment and/or creatinine clearance less than 50 mL/min calculated by Cockcroft-Gault method
- Active malignancy or recent malignancy with chemotherapy treatment within the past 6 months
- Enrollment in any trial and/or use of any investigational product or device within the immediate 30-day period prior to the Baseline visit
- Previous exposure to the investigational product
- Use of prohibited medications
- History or evidence of active tuberculosis (TB) infection at Baseline visit Dose and Mode of Administration:

The study design is shown in FIG. 1. Each cohort consisted of 10 patients; 8 patients were treated with dapansutrile and two patients were treated with placebo. Cohort 1 were treated with 500 mg daily, Cohort 2 were treated with 500 mg twice a day (1000 mg total per day), and Cohort 3 were treated with 500 mg 4 times a day (2000 mg total per day), from Day 1 to Day 14. The study protocol was shown in FIG. 2. Fasting glucose of each patient was tested at Day 1 (baseline), Day 4, Day 8, Day 14, and Day 28.

Results

Among the 30 patients, 19 of them are identified as diabetes mellitus based on medical history, which is common in heart failure patients. The glucose fasting results of the 19 diabetes subjects at Day 14 and Day 28 are summarized in Table 1. Table 1 shows the change of glucose value on Day 14 (last day of treatment) and on Day 28 from baseline level for dapansutrile-treated subjects at 500 mg, 1000 mg, and 2000 mg, pooled all treated subjects, and pooled placebo subjects. The results show a trend of dose response to dapansutrile treatment. At the 2000 mg treatment, the mean fast glucose level decreased 43.5 mg/dL from the baseline level. On Day 14, all dapansutrile-treated subjects showed a statistically significant decrease of glucose level from the baseline level glucose level with a p value of 0.029. On Day 28, which is 14 days after the last treatment, the drug effect was gone.

TABLE 1

| Fasting Glucose Level (mg/dL) in 19 diabetic patients | | | | | |
|---|---|---|---|---|---|
| Visit Statistics | Dapansutrile 500 mg (N = 6) | Dapansutrile 1000 mg (N = 4) | Dapansutrile 2000 mg (N = 4) | All Dapansutrile Subjects (N = 14) | Pooled Placebo Subjects (N = 5) |
| Day 14 - Change from Baseline | | | | | |
| n | 6 | 4 | 4 | 14 | 5 |
| Mean (SD) | −20.0 (36.50) | −16.5 (33.53) | −43.5 (30.05) | −25.7 (33.45) | −9.0 (107.58) |
| Median | −18.5 | −16.5 | −47.5 | −32.5 | −7.0 |
| Percentiles 25th, 75th | −45.0, 16.0 | −45.5, 12.5 | −66.5, −20.5 | −47.0, 11.0 | −10.0, −2.0 |
| Min, Max | −74.0, 20.0 | −47.0, 14.0 | −74.0, −5.0 | −74.0, 20.0 | −165.0, 139.0 |
| p-value* | 0.313 | 0.625 | 0.125 | 0.029 | 0.438 |
| Day 28 - Change from Baseline | | | | | |
| n | 6 | 4 | 4 | 14 | 5 |
| Mean (SD) | 25.8 (82.76) | 7.3 (34.80) | −18.0 (31.57) | 8.0 (59.15) | −51.8 (92.63) |
| Median | −1.5 | −7.0 | −21.5 | −8.0 | 3.0 |
| Percentiles 25th, 75th | −28.0, 26.0 | −12.5, 27.0 | −43.0, 7.0 | −28.0, 21.0 | −101.0, 6.0 |
| Min, Max | −29.0, 189.0 | −16.0, 59.0 | −50.0, 21.0 | −50.0, 189.0 | −192.0, 25.0 |
| p-value* | 1.000 | 0.875 | 0.375 | 0.681 | 0.813 |

Example 2. Clinical Study (Prophetic Example)

Objectives: To demonstrate the efficacy of dapansutrile treatment compared to placebo in HbA1c (glycated hemoglobin) reduction at 26 weeks.

Methodology:

The study is a multi-center, randomized, parallel group, placebo-controlled, clinical trial to evaluate the benefit of 2000 mg/day of dapansutrile compared to placebo among patients with type-2 diabetes mellitus.

Main Criteria for Inclusion:

Patients eligible for inclusion in this study must fulfill all of the following criteria:

- Diagnosis of type 2 diabetes mellitus (American Diabetes Association criteria).
- Age ≥18 years at screening.
- HbA1c levels of 7.5% to 10.5%.
- CRP ≥2 mg/L
- Presence of at least one of the following: history of heart failure or NTproBNP>125 mg, diabetic retinopathy with sign of macular edema on OCT or microangiopathy in angiography, GFR≤60 GFR ml/min/1.7 or macroalbuminuria (≥300 mg/24 h)
- Willingness to maintain diet and exercise regimen during the trial.

Main Criteria for Exclusion:

Patients fulfilling any of the following criteria are not eligible for inclusion in this trial:

- Pregnant or nursing (lactating) women, where pregnancy is defined as the state of a female after conception and until the termination of gestation, confirmed by a positive hCG laboratory test (>5 mIU/ml)
- Nephrotic syndrome or kidney transplant (regardless of renal function)
- Known active or recurrent hepatic disorder (including cirrhosis, hepatitis B and hepatitis C, or confirmed ALT/AST levels >3 times ULN or total bilirubin >2 times ULN)
- Recreational drug use and alcohol dependence that would interfere with the conduct of the trial.
- Known history of allergy or reaction to any component of the investigational product formulation.
- Concomitant treatment with GLP-1 agonists or SGLT2 inhibitors
- Any drugs targeting the immune system (for example, TNF blockers, anakinra, rituximab, abatacept, tocilizumab or steroid hormones)
- Any life-threatening condition with life expectancy <5 years, other than vascular disease that might prevent the patient from completing the study.

Dose and Mode of Administration:

Subjects are randomly assigned to either 2000 mg/day dapansutrile or placebo. Each patient is treated with either dapansutrile or placebo daily for 26 weeks. Blood is drawn for testing pre-dose at Day 1, Day 2, then once a month, and after the last treatment.

Clinical Trial Duration:

The trial duration is 26 weeks.

Clinical Activity Outcomes for Evaluation:

Primary efficacy outcome measure is:

HbA1C

Secondary efficacy outcome measures are:

Stimulated C-peptide (peak, AUC) after a standardized mixed meal or OGT (0-Linked N-Acetylglucosamine (GlcNAc) Transferase) with bolus glucose, +arg/+ glucagon.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for treating diabetes, comprising the step of: administering to a subject suffering from diabetes an effective amount of dapansutrile, or a pharmaceutically acceptable solvate thereof.

2. The method according to claim 1, wherein said method lowers hemoglobin A1C (HbA1c) level in the blood of the subject.

3. The method according to claim 1, wherein said method lowers the blood glucose level in the subject.

4. The method according to claim 1, wherein said method further prevents disease progression by treating microvascular inflammation in the subject.

5. The method according to claim 1, wherein the subject has heart failure.

6. The method according to claim 1, wherein dapansutrile is administered by systemic administration.

7. The method according to claim 1, wherein dapansutrile is administered by oral administration.

8. The method according to claim 7, where dapansutrile is administered 500-4000 mg/day.

* * * * *